United States Patent
Adamzik et al.

(10) Patent No.: US 8,524,937 B2
(45) Date of Patent: Sep. 3, 2013

(54) PROCESS FOR PREPARING POLYOL ESTERS

(75) Inventors: Michael Adamzik, Hünxe (DE); Thomas Müller, Dinslaken (DE); Willy Schulz, Voerde (DE); Heyko Jürgen Schultz, Bottrop (DE)

(73) Assignee: Oxea GmbH, Oberhausen (DE)

( * ) Notice: Subject to any disclaimer, the term of this patent is extended or adjusted under 35 U.S.C. 154(b) by 344 days.

(21) Appl. No.: 12/924,824

(22) Filed: Oct. 6, 2010

(65) Prior Publication Data

US 2011/0087045 A1      Apr. 14, 2011

(30) Foreign Application Priority Data

Oct. 8, 2009   (DE) .................. 10 2009 048 772

(51) Int. Cl.
*C07C 69/003*   (2006.01)

(52) U.S. Cl.
USPC ............................ 560/98; 560/183

(58) Field of Classification Search
USPC ................................... 560/183, 98
See application file for complete search history.

(56) References Cited

U.S. PATENT DOCUMENTS

| | | | |
|---|---|---|---|
| 2,469,446 A | 5/1949 | Strauss | 260/410.6 |
| 2,628,249 A | 2/1953 | Bruno, Jr. | 260/475 |
| 5,142,071 A * | 8/1992 | Kluesener et al. | 554/172 |
| 5,318,790 A * | 6/1994 | Houston et al. | 426/423 |
| 5,324,853 A | 6/1994 | Jones et al. | 560/98 |
| 5,397,494 A * | 3/1995 | Vega et al. | 510/536 |
| 6,423,856 B1 * | 7/2002 | Springer et al. | 554/173 |
| 6,939,980 B2 * | 9/2005 | Memita et al. | 554/170 |
| 6,995,232 B2 * | 2/2006 | Howie et al. | 528/295.5 |
| 7,326,804 B2 * | 2/2008 | Kim et al. | 560/129 |
| 7,579,493 B2 * | 8/2009 | Gutsche et al. | 554/174 |

FOREIGN PATENT DOCUMENTS

| | | |
|---|---|---|
| DE | 199 40 991 | 1/2001 |
| DE | 102 57 525 | 7/2004 |
| JP | 2002-293758 | * 10/2002 |
| WO | WO 94/18153 | 8/1994 |

OTHER PUBLICATIONS

EPO Search Report.
Ullmann's Encyclopaedia of Industrial Chemistry, 5th edition, 1985, VCH Verlagsgesellschaft, vol. A1, pp. 305-319; 1990, vol. A15, pp. 438-440; Kirk Othmer, Encyclopaedia of Chemical Technology, 3rd edition, John Wiley & Sons, 1978, vol. 1, pp. 778-787; 1981, vol. 14, pp. 496-498; Goldsmith, Polyhydric Alcohol Esters of Fatty Acids, Chem. Rev. 33, 257 ff. (1943); and Johnson (edit.). Fatty Acids in Industry (1989) Chapter 9 Polyoxyethylene Esters of Fatty Acids.

* cited by examiner

*Primary Examiner* — Johann R Richter
*Assistant Examiner* — Pancham Bakshi
(74) *Attorney, Agent, or Firm* — Michael W. Ferrell

(57) ABSTRACT

The present invention relates to a process for preparing polyol esters by reacting polyols with linear or branched aliphatic monocarboxylic acids having 3 to 20 carbon atoms by partial recycling of the aliphatic monocarboxylic acid removed into the esterification reaction or into subsequent esterification batches.

34 Claims, No Drawings

PROCESS FOR PREPARING POLYOL ESTERS

CLAIM FOR PRIORITY

This application is based on German Application No. 10 2009 048 772.7, entitled "Verfahren zur Herstellung von Polyolestern", filed Oct. 8, 2009, the priority of which is hereby claimed and the disclosure of which is incorporated herein by reference.

TECHNICAL FIELD

The invention relates to a process for preparing polyol esters from linear or branched aliphatic monocarboxylic acids having 3 to 20 carbon atoms and polyols by converting the starting compounds with partial recycling of the aliphatic monocarboxylic acids.

BACKGROUND OF INVENTION

Esters of polyhydric alcohols, also known as polyol esters, find a variety of uses on a large scale in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopaedia of Industrial Chemistry, 5th edition, 1985, VCH Verlagsgesellschaft, Vol. A1, pages 305-319; 1990, Vol. A15, pages 438-440, or in Kirk Othmer, Encyclopaedia of Chemical Technology, 3rd edition, John Wiley & Sons, 1978, Vol. 1, pages 778-787; 1981, Vol. 14, pages 496-498.

The use of polyol esters as lubricants is of great industrial significance, and they are used particularly for those fields of use in which mineral oil-based lubricants meet the requirements set only incompletely. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4),8(9)-di-hydroxymethyltricyclo[5.2.1.0$^{2,6}$]decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high molecular weight thermoplastic substances, without reacting chemically, preferably by virtue of their swelling and dissolution capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

In order to open up the widest possible fields of use to plasticizers, they must fulfill a series of criteria. They should ideally be odorless, colorless, and light-, cold- and heat-resistant. Moreover, it is expected that they are insensitive to water, comparatively nonflammable and not very volatile, and are not harmful to health. Furthermore, the production of the plasticizers should be simple and, in order to meet ecological requirements, avoid waste substances, such as by-products which cannot be utilized further and wastewaters comprising pollutants. A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the trans-esterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment. Ethylene oxide is a very reactive chemical substance. It can polymerize explosively and forms explosive mixtures with air within very wide mixing ranges. Ethylene oxide irritates the eyes and respiratory pathways, leads to chemical burns and to liver and kidney damage, and is carcinogenic. The handling thereof therefore entails extensive safety measures. Moreover, scrupulous cleanliness of storage apparatus and reaction apparatus has to be ensured, in order to rule out the formation of undesired impurities as a result of side reactions of the ethylene oxide with extraneous substances. Finally, the reaction with ethylene oxide is not very selective, since it leads to mixtures of compounds of different chain length.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycols are prepared at temperatures of 130 to 230° C. over reaction times of 2.5 to 8 hours. To remove the water of reaction, carbon dioxide is used. Suitable catalysts mentioned for the esterification of polyhydric alcohols are inorganic acids, acidic salts, organic sulfonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required.

Both reaction conditions can be made milder by the use of catalysts. In addition to sulfuric acid, organic acids such as p-toluenesulfonic acid and cation exchangers of the polystyrene type are the preferred catalysts. The use of metal powders, such as tin or iron, is also described. According to the teaching from U.S. Pat. No. 2,628,249, color problems in the case of catalysis with sulfuric acid or sulfonic acids can be alleviated when working in the presence of activated carbon.

A procedure in which esters of diethylene glycol and triethylene glycol and of caprylic acid are prepared without addition of catalyst is known from U.S. Pat. No. 2,469,446. The esterification temperature is in the range from 270 to 275° C. and the water of reaction is driven out by means of a carbon dioxide stream.

The reaction regime in which the addition of a catalyst is dispensed with generally works with a molar excess of the particular carboxylic acid, which, owing to its acidity, also acts as a catalyst.

For the removal of the water of reaction formed in the ester formation from the polyol and the carboxylic acids, various processes are known. For example, the water of reaction formed is distilled out of the reaction vessel together with the excess carboxylic acid and passed into a downstream phase separator in which carboxylic acid and water separate according to the solubility properties thereof. In some cases, the carboxylic acid used also forms an azeotrope with water under the reaction conditions and is capable of removing the water of reaction as an entraining agent. Also employed are azeotropic distillation in the presence of an added water-immiscible solvent, heating of the reaction mixture while passing an inert gas through, and the reaction of the polyol and carboxylic acid starting materials under reduced pressure or in the presence of a desiccant. Especially the removal of water by azeotropic distillation has been found to be useful for the establishment of the equilibrium in the preparation of polyol esters. According to the procedure known from DE 199 40 991 A1, the water-immiscible solvent which acts as an entraining agent and which should have a boiling point of less than 112° C. is added to the reaction mixture only on attainment of a temperature of at least 140° C.

The crude ester obtained after removal of the water of reaction and of excess unconverted starting materials, appropriately the carboxylic acid added in excess, can first be treated with an alkaline reagent, for example with an aqueous sodium carbonate or sodium hydroxide solution, in order to remove last residues of acidic constituents. After washing with water and treatment with bleaching earth and activated carbon, last traces of coloring and odorous substances can be removed by applying reduced pressure at elevated temperature.

Processes for working up crude polyol esters are known, for example, from U.S. Pat. No. 2,469,446 A1. In some cases, the treatment with bleaching agents and activated carbon has to be repeated more than once in order to obtain end products with satisfactory color properties.

For the workup of the crude ester, U.S. Pat. No. 5,324,853 A1 proposes removing the excess acid by passing through nitrogen or steam, adding an adsorbent, neutralizing residual organic acid with a base and filtering off solids obtained. The residual amounts of acid present in the filtrate are removed with the passage of steam or nitrogen with simultaneous application of a reduced pressure and recycled back into the esterification reaction. Solids obtained in the vacuum treatment are removed in a final fine filtration. According to the procedure known from DE 199 40 991 A1, the crude ester is dried after alkali treatment, for example by passing an inert gas through the product or applying reduced pressure and optionally additionally distilling under reduced pressure. To improve the color of polyol esters, WO 94/18153 A1 proposes a subsequent treatment with an aqueous hydrogen peroxide solution.

Owing to the quality criteria described at the outset for polyol esters, the process steps in the esterification stage with removal of the water of reaction and in the workup of the crude ester are very important process features, since the adjustment of these process steps significantly influences the sensory and optical properties of the end products. More particularly, high demands are made on the color properties, such as low color number and high color stability, of the polyol esters. The structure of the starting materials, the polyhydric alcohols and the acids, is, in contrast, crucial for the mechanical and thermal properties of the polymer materials plasticized with the polyol esters and influences the hydrolysis and oxidation stability of lubricants.

In the course of preparation of polyol esters, the carboxylic acid used in excess, for example an aliphatic monocarboxylic acid, is removed in the course of the workup process and recycled back into the esterification process. In the continuous process regime, the recycling is effected during the running process, whereas, in the batchwise process, the excess aliphatic monocarboxylic acid removed is first collected and reused in the next batch. For the economic viability of the esterification process, high reuse rates of the aliphatic monocarboxylic acid are desirable. However, this is opposed by the fact that, with increasing reuse, the acid quality suffers as a result of the formation and concentration of by-products, such that the aliphatic monocarboxylic acid recovered has to be at least partly finally discharged and replaced by fresh acid in the course of continuous or batchwise operation. For an economically viable process, it is, however, desirable to use the aliphatic monocarboxylic acid recovered as frequently as possible in the continuous esterification process or, in the case of batchwise operation, in the subsequent production batches, without the quality of the desired polyol ester suffering.

SUMMARY OF INVENTION

It has now been found that, surprisingly, polyol esters can be prepared from polyols and linear or branched aliphatic monocarboxylic acids with an excellent color number and color stability when the aliphatic monocarboxylic acid recovered in the course of workup of the crude esterification mixture is not recycled fully, but only partly, back into the esterification reaction.

The invention therefore consists in a process for preparing polyol esters by reacting polyols with linear or branched aliphatic monocarboxylic acids having 3 to 20 carbon atoms and then working up the reaction mixture by means of steam treatment. The process is characterized in that in a first fraction the aliphatic monocarboxylic acid removed during the reaction is removed fully or partly from the process, in a second fraction the aliphatic monocarboxylic acid still present in the reaction mixture after reaction has ended is removed and recycled fully back into the esterification reaction, and in a third fraction the residual amount of aliphatic monocarboxylic acid removed in the course of steam treatment of the reaction product is removed fully from the process.

The controlled discharge and recycling of the aliphatic monocarboxylic acid obtained during the reaction and subsequent workup phase allows coloring components which form during the esterification reaction to be removed from the process in a simple manner. It has been found that, surprisingly, coloring components can be removed in a first step together with the mixture of water of reaction and aliphatic monocarboxylic acid removed during the esterification reaction. Coloring components in the residual amounts of the aliphatic monocarboxylic acid which are obtained in the course of the workup process in the steam treatment are also accumulated in a third fraction. The aliphatic monocarboxylic acid obtained in the second fraction, which is removed from the crude polyol ester after the esterification reaction, is contaminated only with small amounts of coloring components and can be recycled fully back into the esterification process. In the case of a batchwise process regime, this means that this acid fraction can be reused in subsequent reaction batches.

The inventive procedure can be considered as a fractional distillation of the aliphatic monocarboxylic acid out of the reaction mixture and out of the crude ester obtained. In a first fraction, which may also be referred to as the first runnings fraction, the coloring components accumulate in the mixture of aliphatic monocarboxylic acid and water of reaction, which is removed during the esterification reaction. In a second fraction, which can also be referred to as the intermediate fraction, virtually pure aliphatic monocarboxylic acid is obtained from the crude ester after the esterification reaction has ended, which is contaminated only with a low level of coloring components. In a third fraction, which can also be referred to as the tailings fraction, contaminated aliphatic monocarboxylic acid is again obtained in the course of the steam treatment.

When the process according to the invention is performed batchwise, the aliphatic monocarboxylic acid which is contaminated with coloring components and is obtained as the first runnings fraction in the first fraction and as the tailings fraction in the third fraction is collected and not used for the subsequent production batches. In the case of the continuous process regime, these fractions are discharged continuously and replaced by fresh acid as in the batchwise method or by the less contaminated intermediate fraction from preceding batches. These removed fractions can be collected, purified in a separate distillation step and then used again in the esterification process. The intermediate fraction with a low level of contamination by coloring components or the second fraction is used for the next production batch in the case of the batchwise process regime, or recycled directly into the esterification reactor in the case of the continuous process regime.

The inventive measure of fractional removal and recycling of the excess aliphatic monocarboxylic acid concentrates the coloring components in a small portion of the excess aliphatic monocarboxylic acid used, while the greater residual amount of the aliphatic monocarboxylic acid is substantially free of coloring components. This intermediate fraction with a low level of contamination can be recycled into the esterification process significantly more frequently than all of the contaminated excess aliphatic monocarboxylic acid removed, in which the coloring components are present diluted in a relatively large amount of acid, without the color quality of the desired polyol ester suffering too much. The removal of a small portion of highly contaminated aliphatic monocarboxylic acid and the replacement to the required acid excess by addition of fresh acid or intermediate fractions with a low level of contamination from preceding batches utilizes the aliphatic monocarboxylic acid used to a significantly more productive degree than a procedure in which all of the contaminated aliphatic monocarboxylic acid removed is used again for the esterification reaction without replacement of acid. In this procedure, the entire amount of acid has to be removed from the process and replaced by fresh acid after only a few reuses, in order to obtain polyol ester with adequate color number and color stability.

The reaction between polyol and aliphatic monocarboxylic acid, depending on the starting materials, sets in within the range from about 120 to 180° C. and can be conducted to completion in different ways.

Further features and advantages will become apparent from the discussion which follows.

DETAILED DESCRIPTION

One configuration of the process according to the invention first involves heating proceeding from room temperature to a temperature up to a maximum of 280° C., preferably up to 250° C., and, with the temperature kept constant, lowering the pressure in stages proceeding from standard pressure, in order to facilitate the removal of the water of reaction. The selection of the pressure stages, whether one, two or more than two stages, and of the pressure to be established at the particular stage, may be varied over a wide range and adjusted to the particular conditions. For example, in a first stage, the pressure can be lowered proceeding from standard pressure first down to 600 hPa, and then the reaction can be conducted to completion at a pressure of 300 hPa. These pressure figures are guide values which are appropriately complied with.

In addition to the variation of the pressure, it is likewise also possible to alter the temperature proceeding from room temperature in one, two or more than two stages during the esterification reaction, such that, at constant pressure, the temperature is increased from stage to stage, typically up to a maximum temperature of 280° C. However, it has been found to be appropriate to heat to a maximum of 280° C. with the temperature rising from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. On attainment of the temperature stage of 190° C., the pressure is lowered once again down to 300 hPa, and the esterification reaction is conducted to completion at a temperature up to 250° C. These temperature and pressure figures are guide values which are appropriately complied with. The temperature and pressure conditions to be established at the particular stages, the number of stages and the particular temperature increase or pressure reduction rate per unit time can be varied over a wide range and adjusted in accordance with the physical properties of the starting compounds and of the reaction products, the temperature and pressure conditions of the first stage being established proceeding from standard pressure and room temperature. It has been found to be particularly appropriate to increase the temperature in two stages and to lower the pressure in two stages.

The lower limit of the pressure to be established depends on the physical properties, such as boiling points and vapor pressures, of the starting compounds and of the reaction products formed, and is also determined by the available plant apparatus. Proceeding from standard pressure, it is possible to work in stages within these limits, with pressures decreasing from stage to stage. The upper temperature limit, typically 280° C., should be complied with in order to prevent the formation of decomposition products, which adversely affect color among other properties. The lower limit of the temperature stages is determined by the reaction rate, which must still be sufficiently high to complete the esterification reaction within an acceptable time. Within these limits, it is possible to work in stages with temperatures rising from stage to stage.

The water of reaction formed is distilled out of the reaction vessel in the course of the reaction together with the excess monocarboxylic acid and passed into a downstream phase separator in which the monocarboxylic acid and water separate according to their solubility properties. The monocarboxylic acid used may also form an azeotrope with water under the reaction conditions and be capable of removing the water of reaction as an entraining agent. The progress of the reaction can be monitored by the water obtained. The water which separates out is removed from the process, while the monocarboxylic acid from the phase separator flows back into the reaction vessel. The addition of a further organic solvent, such as hexane, 1-hexene, cyclohexane, toluene, xylene or xylene isomer mixtures, which assumes the task of the azeotroping agent, is not ruled out, but restricted to a few exceptional cases. The azeotroping agent can be added as early as the start of the esterification reaction or on attainment of relatively high temperatures. When the theoretical amount of water expected has been obtained or the hydroxyl number, for example determined according to DIN 53240, has fallen below a fixed value, the reaction is ended by allowing the reaction mixture to cool.

The aliphatic monocarboxylic acid which accumulates in the phase separator after the reaction has ended can be referred to as the first fraction and is contaminated with coloring components. This fraction is removed from the process and purified in a separate acid distillation.

The reaction mixture obtained after the reaction has ended comprises, as well as the polyol ester as the desired reaction product, excess and unconverted aliphatic monocarboxylic acid. The latter is distilled out of the crude product, appropriately with application of a reduced pressure. The distillation conditions to be established appropriately are determined by the physical properties of the polyol used and of the aliphatic monocarboxylic acid, and can be determined by simple preliminary tests. For example, temperatures up to 200° C. and pressures less than 300 hPa, preferably less than 50 hPa, are employed. The aliphatic monocarboxylic acid obtained can be considered as the second fraction or intermediate fraction. It is contaminated only with a low level of coloring components and can therefore be recycled directly back into the esterification process or collected as a starting material for a further batch.

The reaction of polyols and aliphatic monocarboxylic acids can be performed without use of a catalyst. This variant of the reaction has the advantage that it avoids adding extraneous substances to the reaction mixture, which can lead to undesired contamination of the polyol ester. However, it is generally necessary in that case to maintain higher reaction temperatures because only in this way is it ensured that the reaction proceeds at a sufficient, i.e. economically acceptable, rate. In this context, it should be noted that the increase in the temperature can lead to thermal damage to the polyol ester. It is therefore not always possible to avoid the use of a catalyst which facilitates the reaction and increases the reaction rate. Frequently, the catalyst may be an excess of the aliphatic monocarboxylic acid, which is simultaneously a reaction component of the polyol, such that the reaction proceeds autocatalytically. Otherwise, the customary esterification catalysts are suitable for influencing the reaction rate, such as sulphuric acid, formic acid, polyphosphoric acid, methanesulfonic acid or p-toluenesulfonic acid, and likewise combinations of such acids. It is likewise possible to use metallic catalysts, such as titanium-, zirconium- or tin-containing catalysts, for example the corresponding alkoxides or carboxylates. It is also possible to use catalytically active compounds which are insoluble in the reaction system and solid under reaction conditions, such as alkali metal or alkaline earth metal hydrogensulfate, for example sodium hydrogensulfate. Solid catalysts are removed from the reaction mixture after the esterification has ended by simple filtration together with any adsorbent present. The amount of the catalyst used can extend over a wide range. It is possible to use 0.001% by weight up to 5% by weight of catalyst, based on the reaction mixture. Since greater amounts of catalysts, however, give barely any advantages, the catalyst concentration is typically 0.001 to 1.0% and preferably 0.01 to 0.5% by weight, based in each case on the reaction mixture. Appropriately, a decision is made for each individual case, optionally by preliminary tests, as to whether no catalyst should be employed at relatively high temperature or a catalyst should be employed at relatively low temperature.

The polyol is allowed to react with excess aliphatic monocarboxylic acid, typically without addition of a catalyst, such that the excess aliphatic monocarboxylic acid itself acts as a catalyst. The aliphatic monocarboxylic acid used in excess can also serve as an entraining agent for the water of reaction released, and the water/acid mixture removed is likewise capable of entraining the coloring components. The monocarboxylic acid generally has a lower boiling point than the polyol used and can therefore be removed from the crude ester by distillation in a simple manner. The aliphatic monocarboxylic acid is used in a 10 to 50% molar and preferably in a 20 to 40% molar excess per mole of hydroxyl group to be esterified in the polyol.

In a further configuration of the process according to the invention, the esterification is performed in the presence of an adsorbent. This involves using porous, large-surface area solid materials which are typically used in chemical practice both in laboratory and in industrial plants. Examples of such materials are high-surface area polysilicic acids such as silica gels (silica xerogels), kieselguhr, high-surface area aluminum oxides and aluminum oxide hydrates, mineral materials such as clays, carbonates or activated carbon. Activated carbon has been found to be particularly useful. In general, the adsorbent is suspended in finely divided form in the reaction solution, which is agitated by intensive stirring or by introducing an inert gas. This achieves intimate contact between the liquid phase and the adsorbent. The mass ratio of the liquid phase to adsorbent can be adjusted substantially freely and hence according to the individual requirements. It has been found to be useful to use 0.05 to 30, preferably 0.1 to 5 and especially 0.1 to 1 parts by weight of adsorbent per 100 parts by weight of liquid phase. After the reaction has ended, the adsorbent can be removed from the process and recycled into the esterification vessel and reused. Reuse is possible until the decolorizing power of the adsorbent is exhausted. However, it is also possible to leave the adsorbent in the crude product and to remove it at any convenient stage during the workup process.

It is likewise possible, during the esterification reaction, to pass an inert gas, for example nitrogen, carbon dioxide or the noble gases, through the reaction mixture in order to expel the water of reaction.

After removing the excess aliphatic monocarboxylic acid as the intermediate fraction, the crude ester obtained is subjected to a treatment with steam, which, for example, can be effected in simple form by introducing steam into the crude product. One advantage of the steam treatment is that catalyst still present in the course thereof is destroyed and converted to hydrolysis products which can be filtered off efficiently. If the esterification reaction is performed in the presence of an adsorbent, the adsorbent which is already present facilitates the separation of the catalyst conversion products. Otherwise, it may be found to be advantageous to add the adsorbent at the start of the steam treatment. The presence of an adsorbent during the steam treatment likewise has an advantageous effect on the color and on the color stability of the polyol ester. However, it is also possible to filter off the adsorbent after the esterification reaction has ended and excess starting compounds have been removed, i.e. before performance of the steam distillation.

The steam treatment is generally performed at standard pressure, although the employment of a slightly reduced pressure, appropriately down to 400 hPa, is not ruled out. The steam treatment is effected generally at temperatures of 100 to 250° C., preferably of 150 to 220° C. and especially of 170 to 200° C., and is also guided by the physical properties of the polyol esters to be prepared in each case.

In the process step of steam treatment, it is found to be appropriate to proceed in a very gentle manner during the heating period until the attainment of the working temperature, in order to heat the crude ester to the required temperature of the steam treatment.

The duration of the steam treatment can be determined by routine tests and it is generally performed over a period of 0.5 to 5 hours. Too long a steam treatment leads to an undesired increase in the color number of the polyol ester and should therefore be avoided. An enhanced degradation reaction of the polyol ester to acidic compounds is also observed, the content of which is manifested in a rise in the neutralization number or acid number, for example determined according to DIN EN ISO 3682/ASTM D 1613. In addition, in the case of polyol esters based on other diols, for example triethylene glycol or tetraethylene glycol, undesired degradation of the ether chain may set in. In the case of too short a treatment time, the removal of residual acid and water is not sufficiently effective and the desired polyol ester still has too high an undesired acid number and too high a water content. In the case of excessively short treatment time too, only a minor advantageous effect is observed on the color number of the polyol ester.

The residues of aliphatic monocarboxylic acid removed in the course of steam distillation, which can also be considered as the third fraction or as the tailings fraction, are again contaminated with coloring components and are discharged from the process. This fraction can be purified separately from or together with the aliphatic monocarboxylic acid removed in the first fraction or as the first runnings fraction in a separate distillation stage, and recycled back into the esterification process.

The steam treatment is followed, optionally after filtration of the adsorbent and other solids obtained, by the drying of the polyol ester, for example by passing an inert gas through the product at elevated temperature. It is also possible to simultaneously apply a reduced pressure at elevated temperature and optionally to pass an inert gas through the product. Even without the action of an inert gas, it is possible to work only at elevated temperature or only under reduced pressure. The particular drying conditions, such as temperature, pressure and duration, can be determined by simple preliminary tests. In general, temperatures in the range from 80 to 250° C. and preferably 100 to 180° C., and pressures of 0.2 to 500 hPa, preferably 1 to 200 hPa and especially 1 to 20 hPa, are employed. Thereafter, the crude ester is filtered, if this has not already been done, in order to free it of the solids, the hydrolysis products of the catalyst and the adsorbent, if added in the esterification stage or before the steam treatment. The filtration is effected in conventional filtering apparatus at standard temperature or at temperatures up to 120° C. The filtration can be supported by common filtering aids such as cellulose, silica gel, kieselguhr, or wood flour. However, the use thereof is restricted to exceptional cases.

The measure of fractional removal of the unconverted and excess aliphatic monocarboxylic acid allows the coloring components to be removed from the process in a simple manner, such that the amount of adsorbents which is added to lighten the color in some cases can be reduced.

After the steam treatment or after the drying, a further treatment of the polyol ester with oxidizing agents, for example with an aqueous hydrogen peroxide solution or with ozone or ozone-containing gases, may also be provided instead of a treatment with adsorbents, for example with activated carbon, in order to improve the color number. However, this measure is restricted only to a few exceptional cases. The use of an aqueous hydrogen peroxide solution or of ozone or ozone-containing gases, however, has the advantage over the use of solid adsorbents that additional filtration steps become dispensable.

The aliphatic monocarboxylic acid with only a low level of contamination obtained as the intermediate fraction can be reused more frequently, without this resulting in reductions in the color quality of the desired polyol. When, in contrast, all fractions of aliphatic monocarboxylic acid obtained are combined and recycled into the process, only limited reuse is possible owing to the rising color number of the polyol ester. When, therefore, the color-contaminated acid fractions are removed during the esterification reaction and during the workup according to the inventive procedure, the aliphatic monocarboxylic acid recovered as the second fraction or as the intermediate fraction can be exploited more productively.

In order to establish the desired acid excess based on polyol in the esterification reaction, the intermediate fractions can be collected and recycled back into the esterification process, optionally after further addition of fresh acid, or be used as a starting material for subsequent batches.

Light-colored polyol esters are obtained, which also satisfy the remaining specifications, such as water content, residual acid content, residual content of catalyst constituents and residual content of monoester.

The polyhydric alcohols or polyols used as starting materials for the process according to the invention satisfy the general formula (I)

$$R(OH)_n \qquad (I)$$

in which R is an aliphatic or cycloaliphatic hydrocarbon radical having 2 to 20 and preferably 2 to 10 carbon atoms, and n is an integer of 2 to 8, preferably 2, 3, 4, 5 or 6.

Suitable polyols are likewise compounds of the general formula (II)

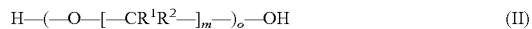

$$H-(-O-[-CR^1R^2-]_m-)_o-OH \qquad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted by the process according to the invention to light-colored polyol esters are, for example, 1,3-propanediol, 1,3-butanediol, 1,4-butanediol, neopentyl glycol, 2,2-dimethylolbutane, trimethylolethane, trimethylolpropane, ditrimethylolpropane, trimethylolbutane, 2,2,4-trimethylpentane-1,3-diol, 1,2-hexanediol, 1,6-hexanediol, pentaerythritol or dipentaerythritol or 3(4),8 (9)-dihydroxymethyltricyclo[5.2.1.0$^{2,6}$]decane.

Useful further polyols include ethylene glycol and 1,2-propylene glycol, and the oligomers thereof, especially di-, tri- and tetraethylene glycol or dipropylene glycol, tripropylene glycol or tetrapropylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-colored polyol esters by the process according to the invention, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexanecarboxylic acid, 2-ethylhexanoic acid, n-nonanoic acid, 2-methyloctanoic acid, isononanoic acid, 3,5,5-trimethylhexanoic acid, 2-propylheptanoic acid, 2-methyl-undecanoic acid, isoundecanecarboxylic acid, tricyclodecanecarboxylic acid and isotridecanecarboxylic acid. The novel process has been found to be particularly useful for the preparation of polyol esters of monoethylene glycol, or of the oligomeric ethylene glycols and of 1,2-propylene glycol, or of the oligomeric propylene glycols with $C_4$- to $C_{13}$- or $C_5$- to $C_{10}$-monocarboxylic acids, and for preparation of polyol esters based on 1,3-butanediol, neopentyl glycol, 2,2,4-trimethylpentane-1,3-diol, trimethylolpropane, ditrimethylolpropane, pentaerythritol or 3(4),8(9)-dihydroxymethyltricyclo[5.2.1.0$^{2,6}$]decane.

The polyol esters of ethylene glycol and the oligomers thereof are outstandingly suitable as plasticizers for all common high molecular weight thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. The preparation process according to the invention makes it possible to prepare, in a simple manner, polyol esters with outstanding color properties which also satisfy further quality demands, such as low odor or a low acid number. The process according to the invention is particularly suitable for preparing triethylene glycol di-2-ethylhexanoate (3G8 Ester), tetraethylene glycol di-n-heptanoate (4G7 Ester), triethylene glycol di-2-ethylbutyrate (3G6 Ester), triethylene glycol di-n-heptanoate (3G7 Ester) or tetraethylene glycol di-2-ethylhexanoate (4G8 Ester).

The process according to the invention can be performed continuously or batchwise in the reaction apparatus typical for chemical technology. Useful apparatus has been found to be stirred tanks or reaction tubes, the batchwise reaction regime being preferred.

The process according to the invention is illustrated in detail in the examples which follow, but it is not restricted to the embodiment described.

WORKING EXAMPLES

Example 1

Preparation of triethylene glycol di-2-ethylhexanoate (3G8 Ester); esterification in the presence of activated carbon with fresh acid The esterification of triethylene glycol with 2-ethylhexanoic acid was performed in a heatable 1 l four-neck flask provided with stirrer, internal thermometer and a water separator.

The flask was initially charged with 250 grams (1.66 mol) of triethylene glycol and 680 grams (4.72 mol) of fresh 2-ethylhexanoic acid, and also 0.4% by weight of activated carbon, based on the overall reaction mixture. While stirring and applying a slightly reduced pressure of 900 hPa, the mixture was heated to 225° C. On attainment of this temperature, the pressure was reduced stepwise to 400 hPa, and water of reaction formed was removed on the water separator, while 2-ethylhexanoic acid flowed back into the reaction vessel. The course of the reaction was monitored by continuously weighing the water discharged via the water separator and by the course of the hydroxyl number. After a total of 14.5 hours of reaction time, the reaction was ended at a residual hydroxyl number of 4.2 mg KOH/g (according to DIN 53240).

In the water separator, after the esterification reaction had ended, 13.3 g of 2-ethylhexanoic acid were obtained as the first fraction. This fraction was not used for the next esterification batch.

Subsequently, the excess 2-ethylhexanoic acid was distilled off at a temperature of 200° C. and at a pressure of 20 hPa over a period of 3.75 hours. 187.1 g of 2-ethylhexanoic acid were obtained as the intermediate fraction, which was reusable for subsequent esterification batches.

There followed a steam distillation at 200° C. and at standard pressure over a period of 2.5 hours. In addition to the amount of water obtained, as the third fraction, a residual amount of 2-ethylhexanoic acid of 0.7 g was also recovered, which was likewise not used for subsequent esterification batches.

After final filtration to remove the activated carbon, light-colored triethylene glycol di-2-ethylhexanoate with the color number reported in Table 1 was obtained.

Example 2

Preparation of triethylene glycol di-2-ethylhexanoate (3G8 Ester); esterification in the presence of activated carbon, reuse of the intermediate fraction from preceding esterification batches Example 2 was performed analogously to example 1, with the sole exception that, instead of fresh 2-ethylhexanoic acid, the 2-ethylhexanoic acid intermediate fraction collected from preceding esterification batches was used.

Example 3

Comparative Example

Preparation of triethylene glycol di-2-ethylhexanoate (3G8 Ester); esterification in the presence of activated carbon, reuse of all of the return acid from preceding esterification batches.

Example 3 was performed analogously to example 2, with the sole exception that, instead of the 2-ethylhexanoic acid intermediate fraction, all of the 2-ethylhexanoic acid recovered from the preceding esterification batches was used.

The color numbers of the worked-up triethylene glycol di-2-ethylhexanoate esters obtained according to examples 1 to 3 are listed in table 1 below. The ester contents determined by gas chromatography and the other indices, such as residual acid content or water content, were in agreement.

TABLE 1

Color numbers of triethylene glycol di-2-ethylhexanoate, prepared according to Examples 1, 2 and 3

|  | Example 1 | Example 2 | Example 3 |
|---|---|---|---|
| Hazen color number (DIN ISO 6271) | 24 | 15 | 45 |

The inventive measure of recycling the aliphatic monocarboxylic acid recovered in the esterification partially into the esterification stage or using it partially for subsequent esterification batches allows polyol esters to be obtained with outstanding color number, which enables the use thereof in a multitude of applications.

While the invention has been described in detail, modifications within the spirit and scope of the invention will be readily apparent to those of skill in the art. In view of the foregoing discussion, relevant knowledge in the art and references discussed above, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. Process for preparing polyol esters by reacting polyols with linear or branched aliphatic monocarboxylic acids having 3 to 20 carbon atoms and then working up the reaction mixture by means of steam treatment, characterized in that in a first fraction the aliphatic monocarboxylic acid removed during the preparation of the polyol ester is removed fully or partly from the process, in a second fraction the aliphatic monocarboxylic acid still present in the reaction mixture after reaction has ended is removed and recycled fully back into the esterification reaction, and in a third fraction the residual amount of aliphatic monocarboxylic acid removed in the course of steam treatment of the reaction product is removed fully from the process.

2. Process according to claim 1, characterized in that the reaction of the starting compounds involves heating to a temperature up to a maximum of 280° C. and lowering the pressure stepwise with the temperature kept constant.

3. Process according to claim 1, characterized in that the reaction of the starting compounds involves heating at constant pressure stepwise up to a maximum temperature of 280° C.

4. Process according to claim 1, characterized in that the reaction of the starting compounds involves heating at a temperature rising stepwise to a maximum of 280° C., and also lowering the pressure stepwise.

5. Process according to claim 4, characterized in that the reaction of the starting compounds involves allowing them to react in a first step at a temperature up to 190° C. and at a pressure up to 600 hPa, and conducting the reaction to completion in a second step by increasing the temperature up to 250° C. and at a pressure up to 300 hPa.

6. Process according to claim 1, characterized in that the reaction of the starting compounds is performed in the presence of a catalyst.

7. Process according to claim 6, characterized in that the catalysts used are catalysts comprising titanium, zirconium or tin.

8. Process according to claim 1, characterized in that the reaction of the starting compounds is performed in the presence of an adsorbent.

9. Process according to claim 8, characterized in that the adsorbent is used in an amount of 0.05 to 30 parts by weight per 100 parts by weight of liquid phase.

10. Process according to claim 8, characterized in that the adsorbent used is silica gel, kieselguhr, aluminum oxide, aluminum oxide hydrates, clays, carbonates or activated carbon.

11. Process according to claim 1, characterized in that the reaction of the starting compounds is performed in the presence of an inert gas.

12. Process according to claim 1, characterized in that the steam treatment is performed at a temperature of 100 to 250° C.

13. Process according to claim 1, characterized in that the polyol ester, after the steam treatment, is dried at temperatures of 80 to 250° C. and at pressures of 0.2 to 500 hPa.

14. Process according to claim 13, characterized in that the polyol ester is dried in the presence of an inert gas.

15. Process according to claim 1, characterized in that the polyol ester is filtered after the steam treatment.

16. Process according to claim 13, characterized in that the polyol ester is filtered after the drying.

17. Process according to claim 12, characterized in that the polyol ester is treated with an oxidizing agent after the steam treatment or after the drying.

18. Process according to claim 17, characterized in that the oxidizing agents used are hydrogen peroxide, ozone or ozone-containing gases.

19. Process according to claim 1, characterized in that the polyols used are compounds of the general formula (I)

$$R(OH)_n \qquad (I)$$

in which R is an aliphatic or cycloaliphatic hydrocarbon radical having 2 to 20 carbon atoms, and n is an integer of 2 to 8.

20. Process according to claim 1, characterized in that the polyols used are compounds of the general formula (II)

$$H-(-O-[-CR^1R^2-]_m-)_o-OH \qquad (II)$$

in which $R^1$ and $R^2$ are each independently hydrogen, an alkyl radical having 1 to 5 carbon atoms or a hydroxyalkyl radical having 1 to 5 carbon atoms, m is an integer of 1 to 10, o is an integer of 2 to 15.

21. Process according to claim 19, characterized in that the polyols used are 1,2-propanediol, 1,3-propanediol, 1,3-butanediol, 1,4-butanediol, neopentyl glycol, 2,2-dimethylolbutane, trimethylolethane, trimethylolpropane, trimethylolbutane, 2,2,4-trimethylpentane-1,3-diol, 1,2-hexanediol, 1,6-hexanediol, pentaerythritol, ethylene glycol or 3(4), 8(9)-dihydroxymethyltricyclo[5.2.1.0$^{2,6}$]decane.

22. Process according to claim 20, characterized in that the polyols used are ditrimethylolpropane, dipentaerythritol, diethylene glycol, triethylene glycol, tetraethylene glycol, dipropylene glycol, tripropylene glycol or tetrapropylene glycol.

23. Process according to claim 1, characterized in that the aliphatic mono-carboxylic acid converted is propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid or 2-propylheptanoic acid.

24. Process according to claim 1 for preparing triethylene glycol di-2-ethylhexanoate, tetraethylene glycol di-n-heptanoate, triethylene glycol di-2-ethylbutyrate, triethylene glycol di-n-heptanoate or tetraethylene glycol di-2-ethylhexanoate.

25. The process according to claim 2, characterized in that the reaction of the starting compounds involves heating to a temperature up to 250° C.

26. Process according to claim 9, characterized in that the adsorbent is used in an amount of 0.1 to 5.0 parts by weight per 100 parts by weight of liquid phase.

27. Process according to claim 26, characterized in that the adsorbent is used in an amount of 0.1 to 1.0 parts by weight per 100 parts by weight of liquid phase.

28. Process according to claim 12, characterized in that the steam treatment is performed at a temperature of 150 to 220° C.

29. Process according to claim 28, characterized in that the steam treatment is performed at a temperature of 170 to 200° C.

30. Process according to claim 13, characterized in that the polyol ester, after the steam treatment, is dried at temperatures of 100 to 180° C. and at pressures of 1 to 200 hPa.

31. Process according to claim 30, characterized in that the polyol ester, after the steam treatment, is dried at temperatures of 100 to 180° C. and at pressures of 1 to 20 hPa.

32. Process according to claim 19, characterized in that the polyols used are compounds of the general formula (I)

$$R(OH)_n \qquad (I)$$

in which R is an aliphatic or cycloaliphatic hydrocarbon radical having 2 to 10 carbon atoms, and n is an integer of 2, 3, 4, 5 or 6.

33. Process according to claim 20, characterized in that the polyols used are compounds of the general formula (II)

$$H-(-O-[-CR^1R^2-]_m-)_o-H \qquad (II)$$

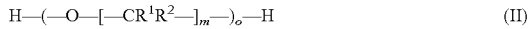

in which $R^1$ and $R^2$ are each independently hydrogen methyl, ethyl, propyl or the hydroxymethyl radical, m is an integer of 1 to 8, o is an integer of 2 to 8.

34. Process according to claim 33, characterized in that the polyols used are compounds of the general formula (II)

$$H-(-O-[-CR^1R^2-]_m-)_o-OH \qquad (II)$$

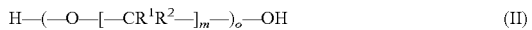

in which $R^1$ and $R^2$ are each independently hydrogen methyl, ethyl, propyl or the hydroxymethyl radical, m is an integer of 1, 2, 3 or 4, o is an integer of 2, 3, 4 or 5.

* * * * *